United States Patent
Cramer et al.

[11] Patent Number: 6,000,844
[45] Date of Patent: Dec. 14, 1999

[54] METHOD AND APPARATUS FOR THE PORTABLE IDENTIFICATION OF MATERIAL THICKNESS AND DEFECTS USING SPATIALLY CONTROLLED HEAT APPLICATION

[75] Inventors: K. Elliott Cramer, Newport News; William P. Winfree, Williamsburg, both of Va.

[73] Assignee: The United States of America as represented by the Administrator of the National Aeronautics and Space Administration, Washington, D.C.

[21] Appl. No.: 08/810,058

[22] Filed: Mar. 4, 1997

[51] Int. Cl.⁶ .................................................. G01N 25/72
[52] U.S. Cl. .................. 374/5; 374/4; 374/124; 374/7
[58] Field of Search .................. 374/4, 5, 124, 374/6, 7

[56] References Cited

U.S. PATENT DOCUMENTS

| | | |
|---|---|---|
| 3,711,718 | 1/1973 | Paul ............................................ 374/6 |
| 3,973,122 | 8/1976 | Goldberg ..................................... 374/4 |
| 4,513,384 | 4/1985 | Rosencwaig ................................ 374/4 |
| 4,647,220 | 3/1987 | Adams et al. . |
| 4,866,276 | 9/1989 | Leavens et al. . |
| 4,916,317 | 4/1990 | Gabriel et al. . |
| 4,950,990 | 8/1990 | Moulder et al. ............................ 374/4 |
| 4,965,451 | 10/1990 | Sölter . |
| 4,988,210 | 1/1991 | Koshihara et al. . |
| 5,111,048 | 5/1992 | Devitt et al. . |
| 5,131,758 | 7/1992 | Heyman et al. ............................ 374/4 |
| 5,168,161 | 12/1992 | Markandey . |
| 5,357,112 | 10/1994 | Steele et al. . |
| 5,358,333 | 10/1994 | Schmidt et al. ............................ 374/7 |
| 5,374,122 | 12/1994 | Devitt et al. . |
| 5,376,793 | 12/1994 | Lesniak . |
| 5,386,117 | 1/1995 | Piety et al. . |
| 5,444,241 | 8/1995 | Del Grande et al. . |
| 5,463,464 | 10/1995 | Ladewski . |
| 5,487,440 | 1/1996 | Seemann . |
| 5,582,485 | 12/1996 | Lesniak ....................................... 374/5 |
| 5,654,977 | 8/1997 | Morris ......................................... 374/4 |
| 5,810,477 | 9/1998 | Abraham et al. ........................... 374/4 |

FOREIGN PATENT DOCUMENTS

| | | | |
|---|---|---|---|
| 48303 | 3/1983 | U.S.S.R. ..................................... | 374/5 |

*Primary Examiner*—Diego Gutierrez
*Assistant Examiner*—Maria Fernandez
*Attorney, Agent, or Firm*—Linda B.B. Blackburn

[57] ABSTRACT

A method and a portable apparatus for the nondestructive identification of defects in structures. The apparatus comprises a heat source (20) and a thermal imager (30) that move at a constant speed past a test surface (10) of a structure. The thermal imager (30) is off set at a predetermined distance from the heat source (10). The heat source (10) induces a constant surface temperature. The imager (20) follows the heat source (10) and produces a video image of the thermal characteristics of the test surface. Material defects produce deviations from the constant surface temperature that move at the inverse of the constant speed. Thermal noise produces deviations that move at random speed. Computer averaging of the digitized thermal image data with respect to the constant speed minimizes noise and improves the signal of valid defects. The motion of thermographic equipment coupled with the high signal to noise ratio render it suitable for portable, on site analysis.

17 Claims, 8 Drawing Sheets

| HOST COMPUTER FUNCTIONS ||
| --- | --- |
| TEST CONTROL | IMAGE CONTROL/PROCESSING |
| 1. Linear Heat Source (20)<br>   a. Start and Stop times<br>   b. Heat Source Intensity<br>   c. Set constant rate of motion.<br>2. Thermal Imager (30)<br>   a. Input constant distance from linear heat source.<br>   b. Control the Start and Stop times and calculate a delay to account for distance of thermal imager (30) from the linear heat source (20).<br>   c. Synchronize imaging with respect to surface area (10) and heat source (20). | 1. Digitize and store video signals.<br>2. Average the video signals with respect to the constant rate of motion.<br>   a. Signals with rate not equal to the inverse of the constant rate (noise) are averaged to a low pixel value.<br>   b. Signals with rate equal to the inverse of the constant rate (valid defect) are averaged to a high pixel value.<br>3. Display |

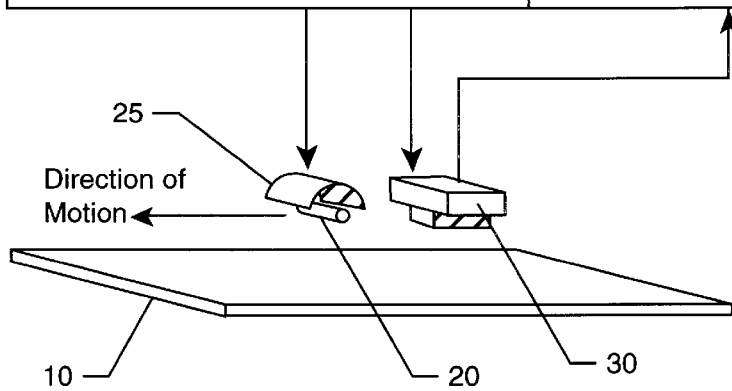

FIG. 3

Thermal Moving Line Image

Conventional Quartz Lamp Thermography

METHOD AND APPARATUS FOR THE PORTABLE IDENTIFICATION OF MATERIAL THICKNESS AND DEFECTS USING SPATIALLY CONTROLLED HEAT APPLICATION

ORIGIN OF THE INVENTION

The invention described herein was made by employees of the United States Government and may be manufactured and used by the government for governmental purposes without the payment of any royalties thereon or therefor.

FIELD OF THE INVENTION

This invention relates generally to nondestructive evaluation and particularly to the on-site detection and real time display of flaws or material loss in a structure by active thermography. The invention further relates to the effective use of a constant speed, portable thermographic unit.

DESCRIPTION OF THE RELATED ART

The purpose of nondestructive testing is to identify the serviceability or quality of an item without removing it from use. A reliable nondestructive test will accurately identify items with defects that render them unfit for use. At the same time, testing increase the confidence in items shown to be free of defects. Well-known items of concern are aircraft, power plant components, or bridges. Hidden defects from causes such as corrosion, production error, or wear could produce a catastrophic failure during use. Because materials, structural defects, and modes of failure vary widely, engineers use different forms of testing to the circumstances. For example, although microwave radiation can reveal cracks in reinforced plastics, it is unable to penetrate metals. Magnetic eddy currents will penetrate thin layers of metals, while gamma ray radiography will show the internal geometry of thicker metals. Accordingly, no single method of nondestructive evaluation will apply to all applications and defects.

Thermography is a subset of nondestructive testing in which the thermal characteristics of an item are analyzed to determine the presence of a defect. Any item with a temperature above absolute zero emits infrared radiation. Active thermography employs an external heat source to induce additional thermal changes in the item; it is particularly effective in a range of applications including testing of brazed joints, identification of material loss or the disbanding of layered material. Passive thermography simply analyzes the existing thermal characteristics of the item tested; it is well suited for medical applications, temperature monitoring, and the detection of abnormal operation of electrical components. Some general challenges to modern thermography include accommodating the varying emissivity within a single material, controlling the temperature of large surfaces, minimizing the typically high number of false readings caused by small signal to noise ratio, and historically expensive equipment (Xavier P. V. Maldague, NON-DESTRUCTIVE EVALUATION OF MATERIALS BY INFRARED THERMOGRAPHY 22 (1993)). The price of thermographic equipment is declining while the quality is improving. Consequently, thermography may be economical for a wider range of applications. Like nondestructive testing as a whole, however, no single method of thermography will apply to all applications.

Many of the advances in thermography try to adapt the laboratory test procedures to the practical needs of the item tested. Indeed, the underlying principles of thermography are well established; the typical apparatus for active thermography includes a sample, a heat source, a heat detector, and some means of analyzing the data collected. One example of a practical need is the ability to test items at their location and minimize off-service time of the tested structure. Some recent inventions disclose means of carrying this apparatus, and perhaps the analysis as well, into the field. A case in point is Koshihara (U.S. Pat. No. 4,988,210), which disclosed a way to transport thermographic equipment within a buried pipe in order to reach the desired location for obtaining a thermal image of the pipe walls. Fundamentally, Koshihara disclosed a thermographic pig directed to overcoming the difficulties of testing an underground pipeline. The test embraces a traditional point-and-shoot procedure, and is therefore unsuited for the coverage of large areas. Further, it does not address the potential for on-site thermal noise. However, the Koshihara disclosure is notable in that it shows how much industry needs on-site thermography.

The prior art discloses a variety of efforts to carry thermography to the field. However, these disclosures face many of the same shortcomings as basic laboratory thermography and do not address the systematic differences inherent in portable, applied thermography. For example, Adams (U.S. Pat. No. 4,647,220) disclosed one such portable thermographic device for detecting corrosion of aircraft. This apparatus included an infrared heat source, a detector for thermal imaging, the capability to vary heat source wavelengths, and a video display. A notable, general advance in this apparatus was the ability to adapt the testing to materials of differing emissivity by changing the wavelength of the heat source. The operator is required to scan the tested material coincident with the application of heat. The thermal response is then displayed by video as a thermal map. The individual components were envisioned as being sufficiently portable so as to be carried by the operator. However, the apparatus is essentially a point and shoot mechanism in which the heat source, detector, and test material remain static until the achievement of the thermal image. Unfortunately, this slows the evaluation of larger surface areas. In addition, it is subject to thermal pollution from other sources. The thermal imaging of the Adams disclosure offers real time depiction of thermal gradients, but no processing to enhance defect signals and minimize thermal noise.

Some inventions contemplate mobility during testing. For example, Leavens (U.S. Pat. No. 4,866,276) disclosed a thermographic apparatus that included a heat source, a thermal detector, a conveyance mechanism, and an analyzing means. The conveyance mechanism was described as a "location means," or wheels that are used to ascertain the location of the thermal detector with respect to the surface of the sample. Thus, the rotation of the wheels mechanically meters relative movement to provide the location of the detector. The detector's output is compared with an empirically derived standard in the form of the thermal response characteristic of the defects of interest. The thermographic apparatus then displays to the operator when the detector output matches the standard. Accordingly, the Leavens disclosure is suited to portable operation directed at larger surface areas, when only a single surface is accessible.

There are several disadvantages to the Leavens disclosure. First, the thermal gradients of all desired defects must be anticipated prior to the test in order to derive the necessary empirically derived standards. Because the analyzing means operates by comparison to a standard, the operator receives merely a digital (yes-no) output. The analyzing means would provide no indication for unanticipated anomalies. Similarly, the Leavens disclosure is subject to thermal noise that might mimic the standard of any of the anticipated defects. Use of a standard also renders the device awkward in the detection of an unpredictable amount of material loss. Curiously, the effect of the speed or acceleration of the apparatus on the heating or on the detection of a particular defect is not accounted for in the analytic process. The movement of the detector is limited to the object of covering surface area. The combination of the first and second disadvantages introduces a third: if depth is an important characteristic of a defect, then the standard thermal gradient of an anticipated defect is valid only for the speed at which the standard was made. That is, the speed of a standard affects the quantity of heat applied to the tested surface. Thus, the operator must reproduce the speed of the standard in order to create valid parameters for comparison to the standard. The analyzing means must also include a library of standards for each defect including thermal gradients for all anticipated speeds. Fourth, the Leaven apparatus provides no direct optical evaluation of variations in the surface temperature. Instead, the analyzing means is limited to the real time comparison or filtering of defect signals. This approach does not allow for noise reduction methods available by image processing. This method seems suited to the detection of a limited number of well defined, expected defects.

Less common are advances that also address the recognized disadvantages of thermography in general, such as thermal noise or minimizing false readings. Some prior inventions have also disclosed the use of photo imaging and computer control in thermography. For example, Devitt (U.S. Pat. No. 5,111,048) discloses an apparatus involving a scanning laser heat source for localized evaluation, an infrared detector, and a graphical display of the temperature gradients produced. The tested surface is preheated to elevated, uniform temperature between 50° C. and 150° C.; then the scanning laser induces localized heating such that defects exhibit a higher radiance than the surrounding surface. A function generator controls the application of heat to ensure complete exposure. Computer based photo imaging enhances defect detection by digitizing signals produced by the temperature gradient.

The Devitt disclosure poses several problems for a portable application. First, the tested structure should remain fixed with respect to the heat source and the detector. Accordingly, testing is limited to the scanning surface until completion of heating and radiance detection. Again, this stop-and-shoot method slows the coverage of surface area and defect detection. Second, this approach to noise presents new difficulties. Because thermal detection occurs in the temperature band between the preheat temperature and that induced by the laser, any noise is limited to that band as well. However, preheating a sample to this extent is a requirement better suited to a laboratory test sample than for the on site testing of an operational component, such as a steam generator tube or an aircraft. At any rate, this step would slow a portable application. If the surface is not preheated, thermal noise remains a problem. Because the Devitt photo imaging is directed simply to storage, comparison, enhancement, and display, thermal noise could potentially pollute data and be enhanced as a false reading. Third, this invention does not take full advantage of computers to control test parameters for signal enhancement or reproducibility. The role of computer based analysis is simply that of photo imaging enhancement.

Another disclosure that addresses a recognized disadvantage of thermography is Lesniak (U.S. Pat. No. 5,376,793). This invention seeks to minimize thermal noise. It uses a heat source that is controlled in order to project a series or pattern of moving bars of infrared radiation onto a portion of a test surface. An infrared detector senses the diffusion of heat from the moving bars; flaws, such as surface cracks or disbanding, resist the diffusion of energy and show up as hot spots. The projected bars move across the area at a constant velocity, such that the heating effect at any one spot is sinusoidal. The infrared detector is correlated to the period of the sinusoidal pattern so that thermal noise, which deviates from the sinusoidal pattern, can be identified and omitted. At the same time, this correlation improves that ability of the infrared detector to detect small deviations from the sinusoidal pattern. Based on that feature, the invention is also able to analyze areas larger than that achieved by other point-and-shoot methods. In general, the Lesniak disclosure is characterized by greater control of the application and detection of heat with a concurrent improvement in the signal to noise ratio.

Although a refinement of conventional point-and-shoot thermography, the Lesniak disclosure is still time consuming. The tested structure should remain fixed with respect to the thermal pattern projector and the detector. Testing is limited to that portion of the surface until completion of the heating and data acquisition. Depending on the sophistication of the embodiment, the operator may also be required to realign the optics for every shot. In addition, forced thermal diffusion requires precise correlation of the detector with the sinusoidal pattern of the projector in order to avoid noise. This correlation, combined with the optical or mechanical control of the projector and detector, could prove expensive and delicate for portable applications.

What is desired is to minimize noise and to speed up portable analysis. Existing methods and apparatus of portable thermography do not conform the test parameters to on-site conditions, such as increased thermal noise. Centralized control of the test parameters would permit reproducibility and improved defect detection. Large surface areas should be tested at a reasonable rate, in order to minimize the time the item is out of service. This method should improve accuracy and overcome difficulties in temperature control of large surface areas.

SUMMARY OF THE INVENTION

It is an object of this invention to identify flaws in single layer and laminated structures. In particular, it is an object of this invention to identify disbanding, cracking, and material loss.

It is an object of this invention to identify such flaws in a manner that is rapid, simple, accurate, and portable.

It is an object of this invention to display defects in a high resolution means, and to reduce the effect of background noise and enhance the effect of valid defect signals.

The above and numerous other objects are achieved by an apparatus that spatially controls the injection of a heat flux into the test material with the thermal imaging of its effect. A heat source and a thermal imager move together at a constant rate, synchronized in such a way as to be accurate with respect to the physical surface of the material and its reaction to the heat source. Controlling these parameters of the thermography limits the potential causes for variance in surface temperature to changes in the thickness of the material. The relative constant movement of a structure by a heat source and a detector joined at a known, fixed distance improves the rate of inspection and the accuracy of defect detection. In the laboratory, such a test involves moving a sample past a fixed heat source and detector (Xavier P. V. Maldague, NONDESTRUCTIVE EVALUATION OF MATERIALS BY INFRARED THERMOGRAPHY 83–85 (1993)). The heat source induces a constant temperature in the test surface that provides a measure of the test material's thickness. Large sample areas of the structure can be exposed and evaluated if the velocity is a known constant. A constant velocity detector is also better able to discriminate valid defects, which pass at the inverse constant velocity of the detector, from noise, which is random. By moving the heat source and detector, these advantages are embodied in an apparatus that is ideal for portable use. On-site, the tested material is typically fixed or too large for movement. Second, this configuration takes advantage of the mobility during testing to cover the surface of the test material at a rate faster than conventional, point-and-shoot thermography. Third, this configuration enables the exploitation of modern photo image processing to reduce noise and improve defect detection.

This approach centers on the creation of a constant surface temperature above ambient such that defects or variations in thickness cause deviations from the constant. An induced temperature of ten degrees above ambient was effective, although other differentials should work. In addition, although variously shaped heat sources will work, a linear source improved the surface thermal response. An infinite linear heat source moving at a constant rate past the surface of a semi-infinite material will create a predictable, constant surface temperature. This temperature is inversely proportional to the thickness of the test material:

$$T(x, z, t) = \frac{q}{\pi K} e^{\left(-v(x-vt)/2\kappa K_O\left[\frac{v((x-vt)^2+z^2)^{1/2}}{2\kappa}\right]\right)}$$

where,
v=the velocity of the moving line source
K=the thermal conductivity
κ=the thermal diffusivity
q=the rate of heat emitted by the line source per unit length
$K_o$=the modified Bessel function of the second kind of order zero.
ρ=the density
c=the specific heat If the material is of thickness L, then the surface temperature will be $$T(x, z, t) = \frac{q}{\pi K} e^{\left(-v(x-vt)/2\kappa\left(K_O\left[\frac{v((x-vt)^2+z^2)^{1/2}}{2\kappa}\right]+2\sum_{n=1}^{\infty} K_O\left[\frac{v((x-vt)^2+(2nL)^2)^{1/2}}{2\kappa}\right]\right)\right)}$$

If the thermal imager's frame of reference centers on the linear heat source, moving with it past the surface at an offset distance, then the surface temperature becomes:

$$T(x, z, t) = \frac{q}{\pi K} e^{\left(-v(x)/2\kappa\left(K_O\left[\frac{v|x|}{2\kappa}\right]+2\sum_{n=1}^{\infty} K_O\left[\frac{v(x^2+(2nL)^2)^{1/2}}{2\kappa}\right]\right)\right)}$$

An imager that follows a linear heat source greater than a distance of $L^{3/2}$, where $Lv/\kappa<25$, will encounter a constant temperature given by $q/(Lv\rho c)$. The constant temperature of the surface is inversely proportional to the thickness of the layer. For a thin layer of material with high diffusivity, the quickly attained constant temperature provides a good measure of the thickness.

The actual temperature encountered could be expected to vary because of approximations to theoretical parameters. For example, a linear heat source is finite, duration of the heating is limited, and the actual thickness of a tested material varies. Such approximations contribute to in-plane heat flow that could cause the surface temperature to fall. To counter the effects of this temperature decay, the thermal imager should follow the heat source closely, offering little time for in-plane heat flow to reduce the temperature.

This procedure requires precise control of the test parameters, for which computer control is ideal. A computer can regulate the constant speed, the number of test cycles, the application and strength of the heat source, when the thermal imager begins, and signal processing. For example, thermal images can be sensed and digitized by pixel for computational manipulation. This precision allows repeated cycles in which the parameters, such as velocity, are sufficiently reliable that the digitized data is suitable for quantitative time based analysis. Computer resources are sufficiently portable to permit such themographic testing of structures on-site.

Computer control also permits real time averaging with respect to the constant speed. Indeed, this form of signal processing enables a full exploitation of the constant speed, mobile configuration. As described above, valid defect signals will pass at the inverse of the constant velocity of heating and imaging, while noise is random. Therefore, the digitized signal of a defect should follow a predictable sequence of pixels at the inverse constant rate. Real-time averaging means that a defect signal will be averaged to a consistently high pixel value. The digitized signal of a defect will follow an unpredictable sequence of pixels. Accordingly, the noise signal will be averaged to a low pixel value because the average will include pixels of no value. Noise can be reduced even further by cyclic repetitions of tests under the same conditions. Real time averaging enhances positive signals and permits the exclusion of random noise.

In conclusion, this apparatus spatially controls the injection of a heat flux into a test material, images the thermal effect, processes the thermal data, and displays the result. Computer control moves the heat source and the thermal imager, which follows at a predetermined, offset distance. Their operation is synchronizing with respect to the location of the test surface. Signal to noise ratio is improved by the combined effects of constant speed, image processing, and real time averaging of the digitized data. The apparatus takes advantage of the mobility of the test apparatus to cover the surface of the test material at a rate faster than conventional, point-and-shoot thermography. In addition, the spatial control of heating overcomes the difficulties of controlling the temperature of a large surface area.

BRIEF DESCRIPTION OF THE DRAWINGS

For a more complete understanding of the present invention, reference should be made to the Description of the Preferred Embodiment below.

FIG. 3 summarizes the function of computer processing and control.

DESCRIPTION OF THE PREFERRED EMBODIMENT

Figure 1:
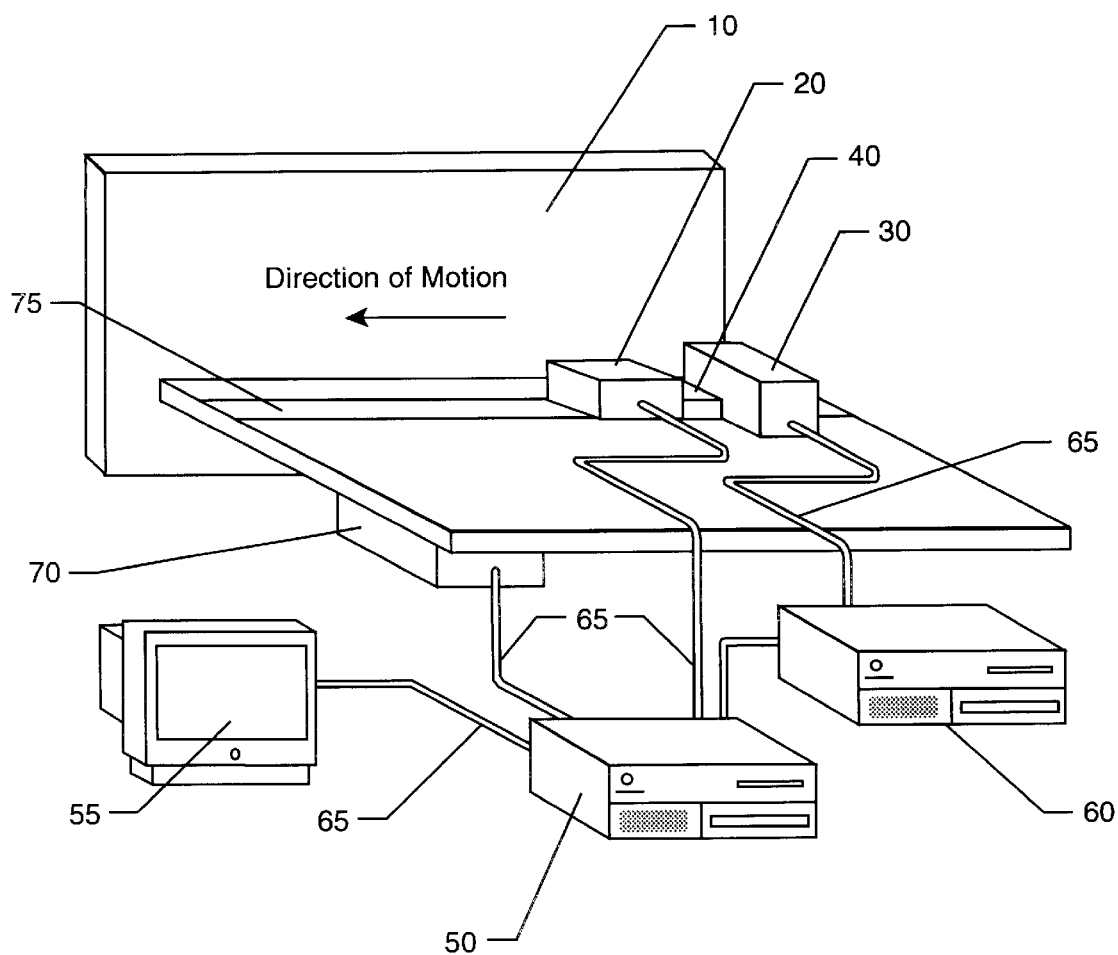
FIG. 1 shows the basic experimental setup of the overall thermographic inspection system.

FIG. 1 illustrates the experimental setup designed to test the portable configuration's ability to detect material flaws in a test surface (10). The heat source (20) was a 1000 watt quartz lamp. The thermal imager (30) was a commercial infrared radiometer with a mechanically scanned HgCdTe (Mercury-Cadmium-Telluride) detector, cooled to near liquid nitrogen temperatures by a closed cycle electric microcooler. The radiometer was capable of detecting a temperature difference of less than 0.1° C. at a range of 8 to 12 micrometers. The radiometer's video frame rate was 30 images per second. The images were in an RS170 format, which is compatible with commercial video equipment. The imager used a 0.5× wide-angle lens and four germanium optical elements to double the systems field-of-view. Thermal imager (30) was fixed behind heat source (20) by a portable member (40), which was capable of being fixed at a variety of distances. As noted above, for a linear heat source, the distance at which the portable member is set should be greater than $L^{3/2}$, where L is the thickness of the test surface (10).

Figure 2:
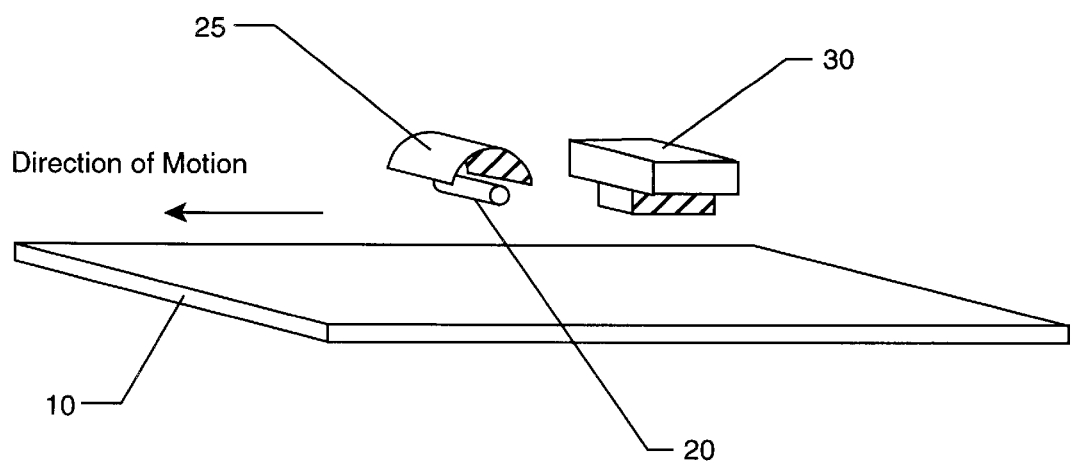
FIG. 2 details the orientation of the thermographic components.

FIG. 2 details the arrangement of test surface (10), heat source (20), and thermal imager (30). The heat source (20) can be a line source, in which case an elliptical reflector (25) can be situated behind the quartz tube to focus the heat into a line. In fact, the experimental setup used a linear heat source (20) with an elliptical reflector (25). As shown in FIG. 2, the heat source (20), the elliptical reflector (25), and the thermal imager (30) move at a constant rate with respect to the test surface (10).

A single, commercially available microcomputer could control this invention, performing the general functions as described in FIG. 3. For ease of configuration, the experimental setup used one computer (50) to host the image processing hardware and to control the invention parameters and a second computer (60) to control radiometric adjustments of the thermal imaging camera (30). First computer (50) controlled the operation of heat source (20), digitally regulated the speed of at which the heat source (20), its elliptical reflector (25), and thermal imager (30) passed over test surface (10). For experimental purposes, a commercially available scanning table (70) was used, capable of speed adjustment to a rate of up to 30.5 cm/sec. This scanning table (70) provided a standard linear scanning bridge (75), which enabled heat source (20), portable member (40), and thermal imager (30) to move at a controlled, constant rate past the test surface (10). First computer (50) also synchronized the application of heat source (20) and the imaging of the radiometric thermal imager (30) by starting each scan a fixed time prior to when second computer (60) began data collection. In addition, first computer (50) provided a video display (55) and storage of the processed video output. Commercially available cabling was sufficient for the experimental setup (65).

In practice, the constant speed motion could be supplied by a variety of means; one example is the AutoCrawler™, which is capable of constant speeds up to 3 feet per second. The AutoCrawler™ was disclosed by Seeman (U.S. Pat. No. 5,487,440), and is capable of moving at a constant speed across surfaces of any orientation using a vacuum (suction cup) track system. This device is merely a vehicle for test or maintenance equipment. One of the anticipated uses of the AutoCrawler™ was for magnetic eddy current testing of aircraft seams and rivets. Magnetic eddy current offered the advantage of continuous, automatic testing. This disclosure introduces a form of thermography also suitable for automatic, continuous testing of large areas.

The first computer (50) hosted image processing hardware. This onboard, commercially available, real-time image processor digitized and stored the video output of the radiometer at standard frame rates. The processor provided eight megabytes of memory for the storage of 16 images of 512×512 16-bit pixels. In addition, the processor could subsample the video data to produce 256 images of 128×128 16-bit pixels, which allowed real-time averaging of the radiometer's digitized video output with respect to the constant speed, as discussed above. The processed images were transfered to its computer (50) for storage and analysis via an input-output card. This card allowed the transfer of both digital and analog data.

Because active thermography seeks to identify a material's response to a known application of heat, radiation from extrinsic sources could impair the thermal image. The emissivity of a plane surface indicates its radiating power in comparison to a black surface. An emissivity equal to a value of one means that the thermal images should be directly proportional to the surface temperature of the material. An emissivity of less than one means that the thermal images will be a combination of surface temperature and background radiation sources. Painting low emissivity surfaces is required to enhance the accuracy of the thermal images. Commercially available, water based, non-toxic paint would suffice. In application, bare aircraft aluminum has an emissivity of less than 0.1; however, standard aircraft paint produces satisfactory emissivity and requires no further emissivity treatment.

Experimentation showed that the mobile configuration was able to provide a better image than static thermography in a much shorter inspection time. Two examinations of laboratory samples supporting this finding are discussed here. An examination of a sample taken from an actual aircraft confirmed these findings.

Figure 4:
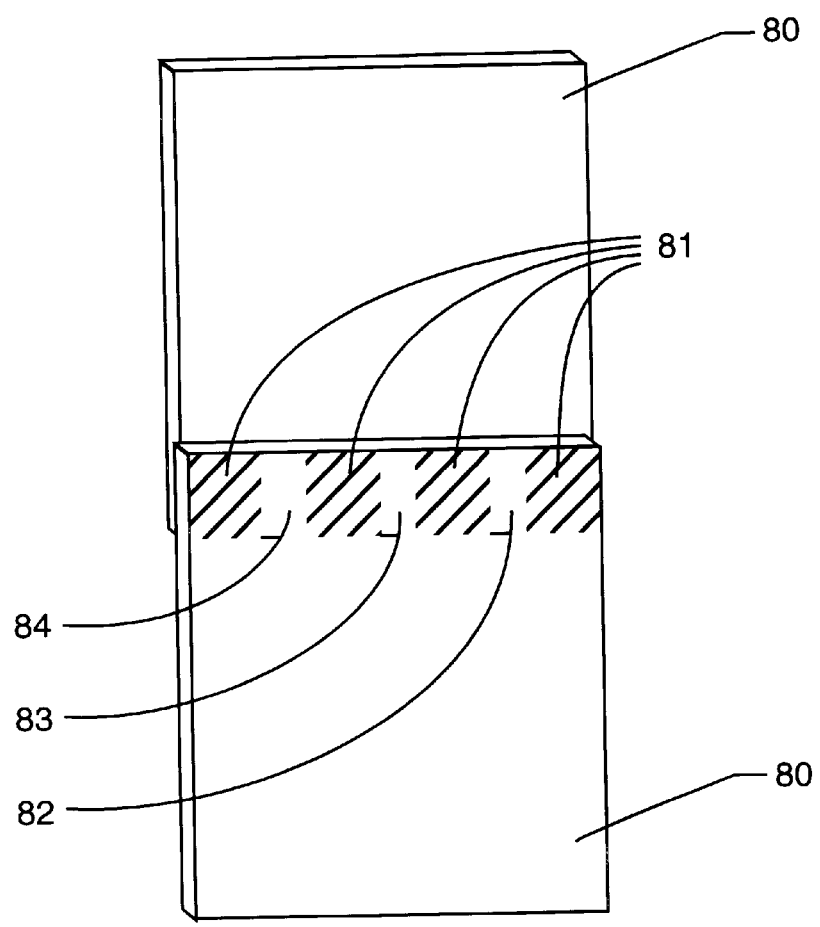
FIG. 4 shows a sample lap joint of two aluminum plates used in experimentation. This lap joint was given three areas of disbanding.
Figure 5A:
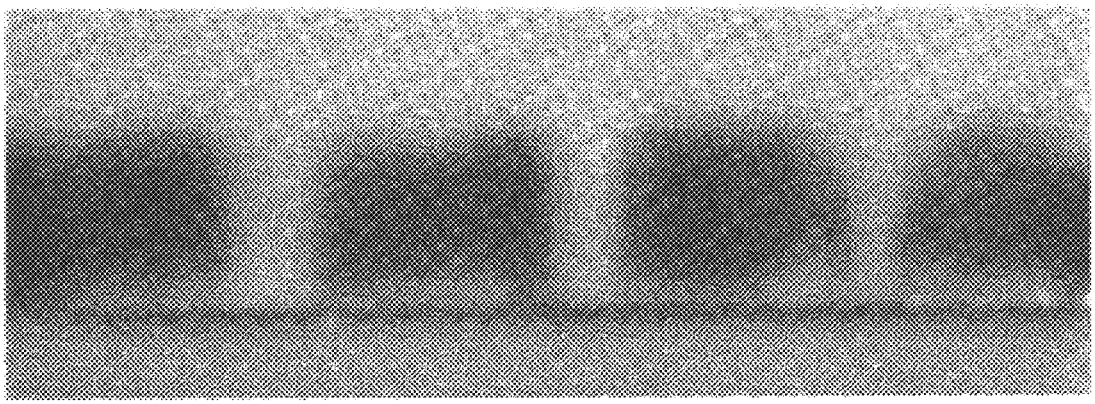
FIG. 5(a) is a black and white photograph of the video output of the mobile configuration inspection that shows the three areas of disbanding in the lap joint of two aluminum plates.
Figure 5B:
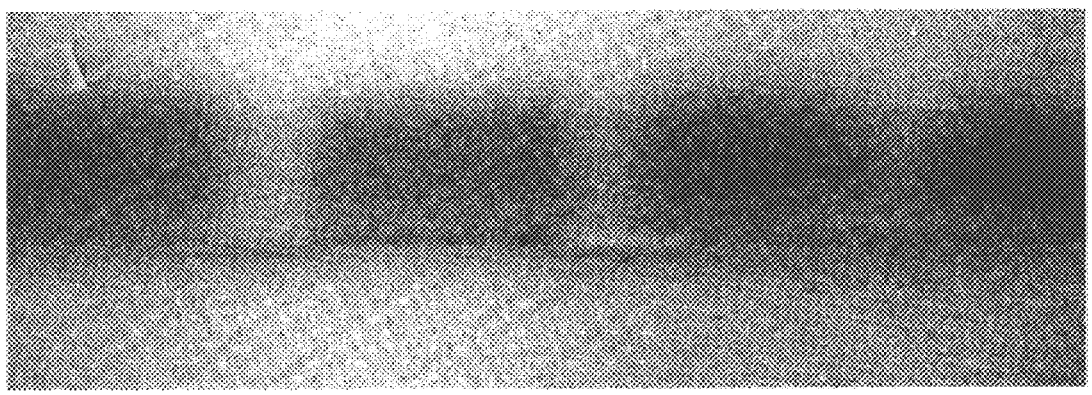
FIG. 5(b) is a black and white photograph of the video output of a conventional, static quartz lamp thermographic analysis of the same lap joint.

One test sample was a lap joint or bond of two 2024-T3 aluminum sheets (80) as shown in FIG. 4. The aluminum sheets (80) were 1.0 mm. thick and overlapped by approximately 7.6 cm (81). A standard two part epoxy provided the bond. The lap joint was given three disbonds or points of delamination, of width measuring 1.27 cm. (82), 2.54 cm. (83), and 3.81 cm (84). The width of the disbonds varied to show accuracy. Each disbond extended from the top to the bottom of the lap joint. FIG. 5(a) is an ordinary black and white photograph of the video output of the mobile configuration. The dark areas show the thermal response characteristic of the greater material thickness at the lap joint. FIG. 5(b) is an ordinary black and white photograph of the video output of a conventional, static quartz lamp thermographic analysis of the first sample. The mobile configuration was able to collect its data in 12 seconds, whereas the less clear, static procedure required 72 seconds. The rapid, mobile configuration showed additional, unintentional disbanding adjacent to the 1.27 cm. (82) disbond.

Figure 6:
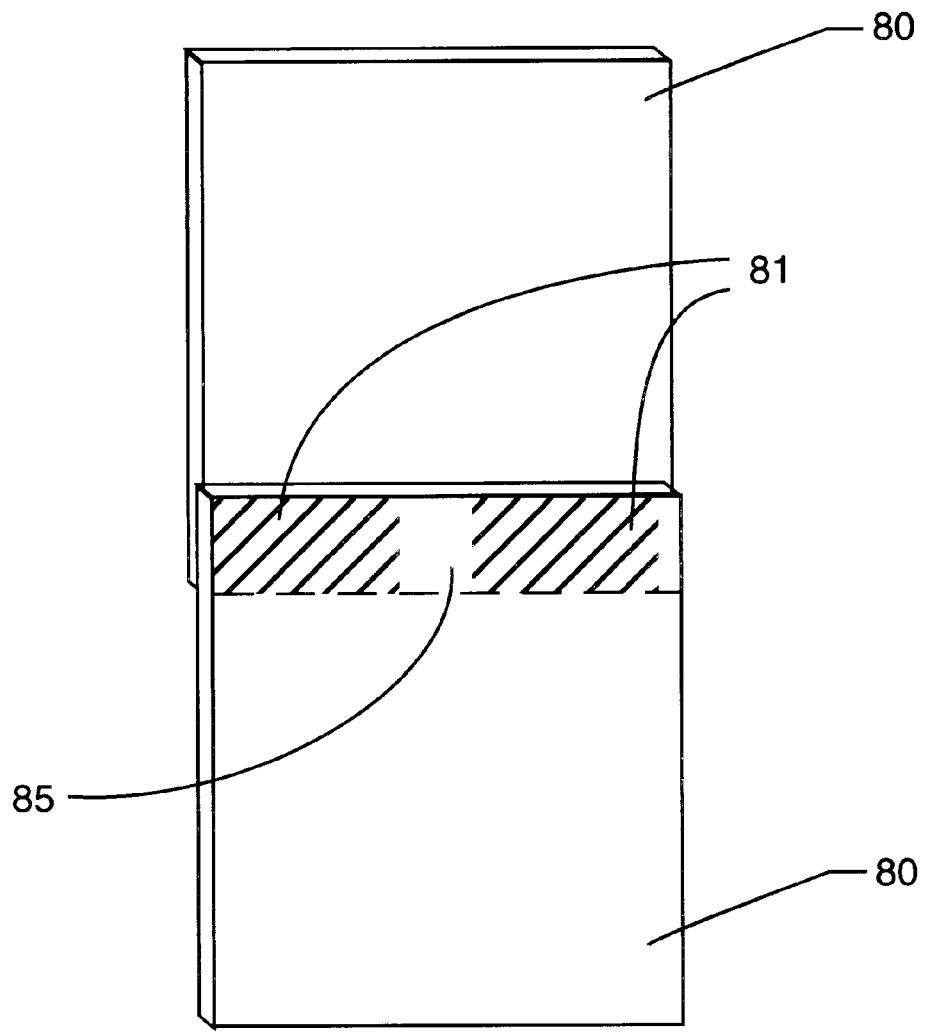
FIG. 6 shows a sample lap joint of two aluminum plates used in experimentation. This lap joint was given one area of 25 percent material loss.
Figure 7:
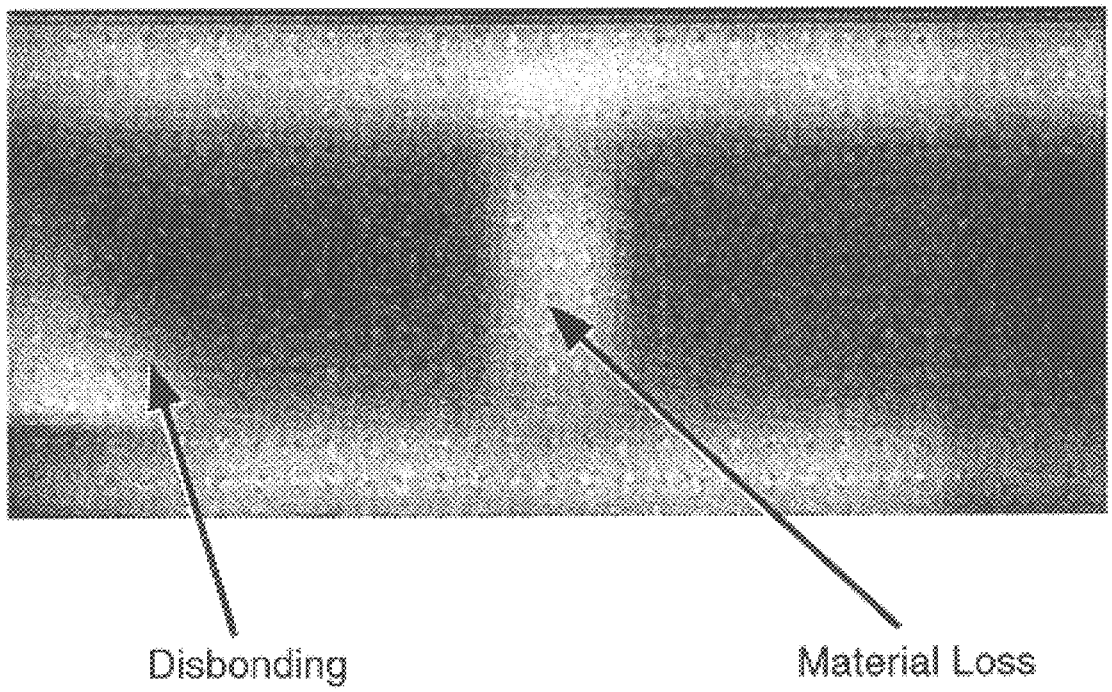
FIG. 7 is a black and white photograph of the video output of the mobile configuration inspection showing the one area of 25 percent material loss in the lap joint.

A second test sample was also a lap joint or bond of two 2024-T3 aluminum sheets (80) as shown in FIG. 6. Here, the lap joint included a single region 2.54 cm. wide (85) in which there was 25 percent loss of material thickness. FIG. 7 is an ordinary black and white photograph of the video output of the mobile configuration analysis. In addition, the analysis revealed a triangular area of disbanding in the corner of the lap joint (86). Conventional static thermography later confirmed this disbond.

Figure 8:
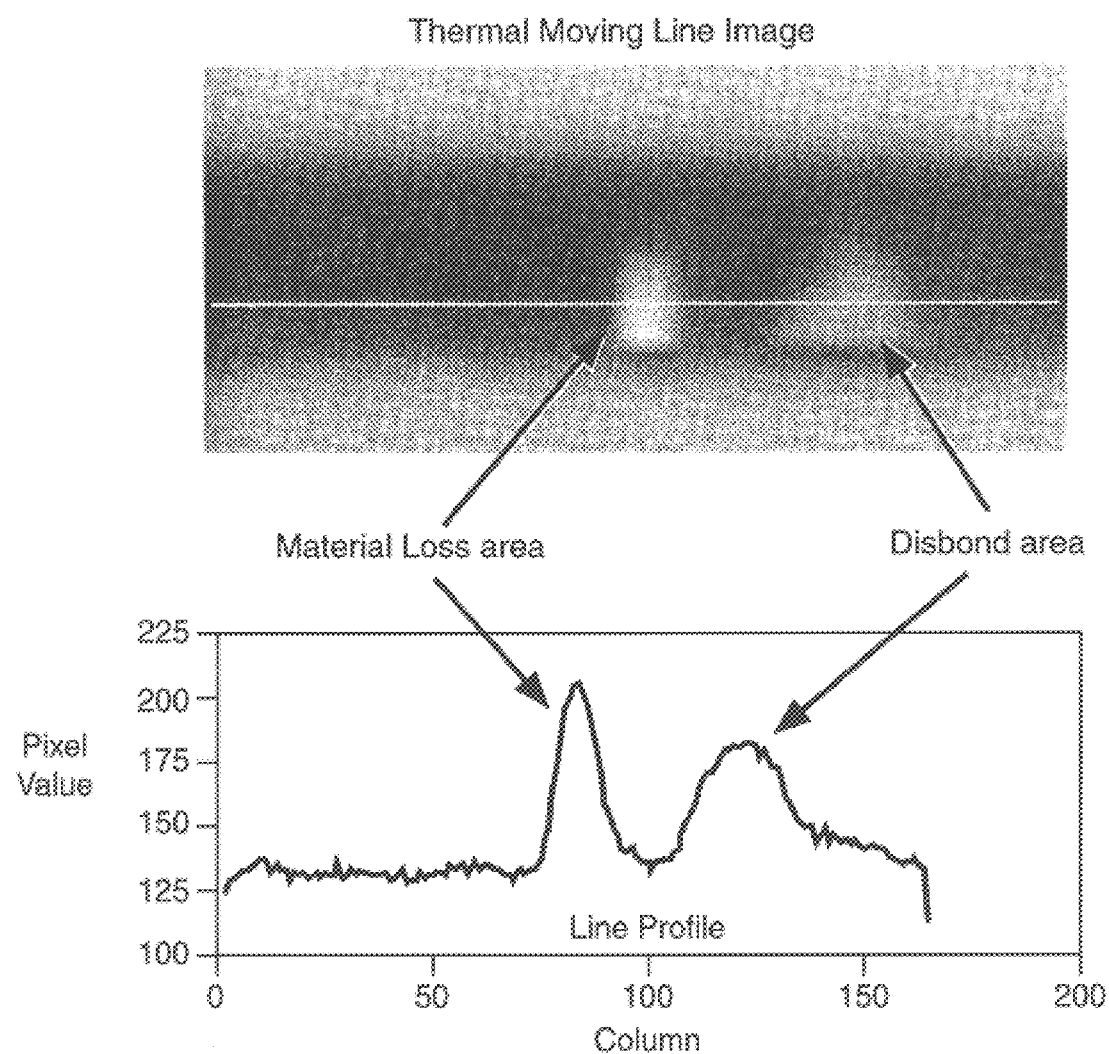
FIG. 8 is demonstrates the ability to graph the digitized thermal response by pixel value across the surface of the test material.

Additional features of the mobile analysis are worth note. First, digitizing the thermal response allows the operator to graph the thermal response by the pixel value across the surface of the test material, FIG. 8. Subsurface characteristics demonstrate typical profiles that can be distinguished by this graph. For example, material loss by corrosion provides an abrupt drop in material thickness, such that the pixel value responds by a spike increase (91). Disbonding of a lap joint is a more gradual decrease in thickness, causing a more gradual increase in pixel value (92). Second, digitization is amenable to quantitative analysis and comparison over time. The strict control of test parameters in this procedure would allow the results of a later analysis to be compared quantitatively to the results of an earlier analysis. Accordingly, the material history could reveal with precision trends of material loss or disbanding. Variations in parameters, such as the quantity of heat applied, could provide information about variances in propagation rates.

Therefore, while the present invention has been disclosed in connection with the preferred embodiment thereof, it should be understood that there may be other embodiments which fall within the spirit and scope of the invention as defined by the following claims.

What is claimed is:

1. A portable, non-destructive method of testing a material for structural defects, comprising the steps of:
   a. directing thermal radiation onto a surface of a tested material to induce a constant surface temperature above ambient;
   b. moving the thermal radiation along the surface of the tested material at a constant rate with respect to said tested material;
   c. thermally imaging the surface of said tested material at a predetermined fixed distance from the thermal radiation, such that the thermal imaging follows the thermal radiation;
   d. recording a plurality of thermal images for a unit area of the tested surface, at a recorded time, that accounts for the constant rate and said predetermined fixed distance between the imaging and the thermal radiation;
   e. converting the thermal images into digital data;
   f. averaging said digital data with respect to the inverse of the constant rate of the thermal radiation and the thermal imaging; and
   g. displaying the averaged digital data in a manner that shows deviation from the constant surface temperature, with respect to the averaged digital data's location on the test surface.

2. The method of claim 1 wherein the thermal radiation is directed linearly onto the surface of a tested material and moves in a direction aligned with the linearity of the thermal radiation.

3. The method of claim 1 wherein the averaging step comprise the additional step of averaging said digital data in real time.

4. An apparatus for the non-destructive detection of structural defects in a test material, comprising:
   a. a portable heating means, for the heating of a surface of a test material to a constant temperature above ambient,
   b. a portable thermal imaging means, for detecting and producing a plurality of thermal images characterizing the thermal radiation of the test material;
   c. a portable means for fixing said portable heating means and said portable thermal imaging means with respect to each other at a predetermined distance, and for moving the heating and the imaging means past a surface of a test material at a constant rate, whereby said portable thermal imaging means follows said portable heating means and detects thermal radiation associated with the heating of said test material;
   d. a means for converting the thermal images to digital data;
   e. a means for averaging the digital data of the plurality of images produced by said portable thermal imaging means with respect to the constant rate at which said portable heating means and said portable thermal imaging means move past the surface of the test material; and
   f. a means for the display of the digital data of the average of the plurality of thermal images in a manner that shows deviation from the constant surface temperature of the test surface, with respect to its location on the test surface.

5. The apparatus of claim 4, further comprising a means for storing the plurality of images characterizing the thermal radiation of the test material.

6. The apparatus of claim 4, further comprising a means for storing the average values of the plurality of images produced by said portable thermal imaging means with respect to the constant rate at which said portable heating means and said portable thermal imaging means move past the surface of the test material.

7. The apparatus of claim 4, wherein said heating means is oriented linearly, so as to apply a line of thermal radiation to the surface of the test material when said heating means is moved in a direction aligned with the linearity of said thermal radiation.

8. The apparatus of claim 7, wherein the heating means employs an elliptical reflector to focus the thermal radiation into a line.

9. The apparatus of claim 7, wherein the heating means is a controllable quartz lamp.

10. The apparatus of claim 4, further comprising a means for accounting for any delay in said portable thermal imaging means reaching a particular location on the tested surface after said portable heating means, caused by the predetermined distance between said portable heating means and said portable thermal imaging means.

11. The apparatus of claim 4, further comprising a means for averaging the digital data of the plurality of images produced by said portable thermal imaging means with respect to the constant rate at which said portable heating means and said portable thermal imaging means move past the surface of the test material a plurality of times, wherein the heating of the surface of the test material, the detection and production of the plurality of thermal images, the rate of movement of the heating and the imaging means past the surface of the test material, and the location of the portable heating means and portable thermal imaging means with respect to the surface of the test material are not varied in each of the plurality of times the portable heating means and the portable thermal imaging means are moved past the surface of the test material.

12. The apparatus of claim 4, wherein said portable thermal imaging means is a mercury, cadmium, telluride radiometric detector.

13. The apparatus of claim 4, wherein said portable thermal imaging means employs wide angle lens to increase the area of the thermal images.

14. The apparatus of claim 4, wherein said means for the display of the average of the plurality of thermal images is capable of displaying the thermal images by pixel value with respect to location on the test surface.

15. A portable, non-destructive method of testing a material for structural defects, comprising the steps of:
   a. directing thermal radiation from a heat source onto a surface of a tested material to induce a constant surface temperature above ambient;
   b. moving the heat source at a rate that is constant with respect to said tested material;
   c. thermally imaging the surface of said tested material with a thermal imager fixed at a predetermined distance from the heat source, such that the thermal imager follows the heat source;
   d. recording a plurality of thermal images for a unit area of the tested surface, at a recorded time, wherein said recording step accounts for the constant rate of movement of said heat source and said predetermined distance between the thermal imager and the heat source;
   e. converting the thermal images into digital data;
   f averaging said digital data with respect to the inverse of the constant rate of movement of said heat source and the thermal imager; and
   g. displaying the averaged digital data in a manner that shows deviation from the constant surface temperature, with respect to the averaged digital data's location on the test surface.

16. The method of claim 15 wherein the thermal radiation is directed linearly onto the surface of a tested material and moves in a direction aligned with the linearity of the thermal radiation.

17. The method of claim 15 wherein the averaging step comprise the additional step of averaging said digital data in real time.

* * * * *